United States Patent
Ark et al.

(10) Patent No.: US 6,949,110 B2
(45) Date of Patent: Sep. 27, 2005

(54) CONNECTOR ASSEMBLY FOR A SURGICAL TOOL

(75) Inventors: Timmon Ark, Charlottesville, VA (US); Daniel L. McCombs, Charlottesville, VA (US)

(73) Assignee: MicroAire Surgical Instruments, Inc., Charlottesville, VA (US)

( * ) Notice: Subject to any disclaimer, the term of this patent is extended or adjusted under 35 U.S.C. 154(b) by 955 days.

(21) Appl. No.: 09/886,371

(22) Filed: Jun. 22, 2001

(65) Prior Publication Data

US 2002/0198556 A1 Dec. 26, 2002

(51) Int. Cl.[7] ............................................. A61B 17/14
(52) U.S. Cl. ...................... 606/178; 606/205; 606/147; 173/217
(58) Field of Search ................................. 606/178, 205, 606/151, 139, 140, 147, 1, 80, 239, 180; 173/217; 81/469, 57.11; 310/47, 50; 604/22

(56) References Cited

U.S. PATENT DOCUMENTS

| | | | | |
|---|---|---|---|---|
| 4,867,158 A | * | 9/1989 | Sugg ............................ | 606/80 |
| 4,995,877 A | * | 2/1991 | Ams et al. ................... | 606/180 |
| 5,480,409 A | * | 1/1996 | Riza ............................. | 606/205 |
| 5,520,634 A | * | 5/1996 | Fox et al. ..................... | 604/22 |
| 5,720,742 A | * | 2/1998 | Zacharias ..................... | 606/1 |
| 5,796,188 A | * | 8/1998 | Bays ............................ | 310/50 |
| 6,220,368 B1 | * | 4/2001 | Ark et al. .................... | 173/217 |
| 6,257,351 B1 | * | 7/2001 | Ark et al. .................... | 173/217 |
| 6,391,046 B1 | * | 5/2002 | Overaker et al. ........... | 606/205 |
| 6,805,700 B2 | * | 10/2004 | Miller ......................... | 606/239 |

* cited by examiner

*Primary Examiner*—Fadi H. Dahbour
(74) *Attorney, Agent, or Firm*—Greenblum & Bernstein, P.L.C.

(57) ABSTRACT

A connector assembly for connecting a surgical saw blade to a housing of a surgical instrument. The connector assembly allows a surgeon to align, insert and lock the surgical blade in the collet of the surgical instrument without any special tools, and further provides a stable and robust platform for mounting the surgical saw blade thereto. The connector assembly includes a cam lever assembly for allowing the user to apply a clamping force to the surgical saw blade with minimum actuation force.

20 Claims, 10 Drawing Sheets

CONNECTOR ASSEMBLY FOR A SURGICAL TOOL

BACKGROUND OF THE INVENTION

1. Field of the Invention

The present invention relates generally to a connector assembly for a surgical instrument and, more particularly, to a connector assembly for securing a surgical tool to a housing of a surgical instrument.

2. Background Description

Connector assemblies in surgical instruments play an important role in the efficacy and safety of the surgical instrument. That is, a surgical instrument will not be deemed safe and effective without a connector assembly which can properly secure the surgical tool to the housing of the surgical instrument. It is with this in mind that manufacturers of surgical instruments give the utmost attention and care to the design and manufacture of connector assemblies.

Connector assemblies are designed to lock the surgical tool to the housing of the surgical instrument. Although many connector assemblies are currently manufactured and sold worldwide for use in surgical instruments, there is certainly concern that many of these connector assemblies do not maintain a secure connection. It is also noted that many of these connector assemblies can only secure a surgical tool to the housing with cumbersome tools, which have a tendency of breaking or being lost. In any of these scenarios, the surgical instrument may be rendered useless, thus requiring the disposal of the surgical instrument.

By way of explanation, in order to mount and secure a surgical tool such as a surgical saw blade to a housing of the surgical instrument it is necessary to place the surgical saw blade into a collet of the surgical instrument. Thereafter, the collet is rotated by a key or a special tool so as to press fit (e.g., friction fit) the surgical saw blade between opposing arms of the collet. However, these type of collets have a tendency to become "stripped" during the mounting of or removal of the surgical saw blade. In the cases when the collet becomes stripped or otherwise rendered inoperable, the surgical instrument must either be discarded or retrofitted with a new collet.

A further shortcoming of press or friction fitting the surgical tool within the collet of the surgical instrument is the fact that the surgical tool can easily become dislodged or loosened during the surgical procedure. This typically happens due to the reciprocating or rotational movement of the surgical tool during the surgical procedure. The loosening or dislodgement of the surgical tool may also be the result of an overused or deteriorated collet, or simply due to the force applied by the surgeon on the surgical instrument during the surgical procedure.

What is thus needed is a connector assembly that is easy to use and which securely mounts and locks the surgical tool to the surgical instrument. Such an assembly would preferably be a keyless system.

SUMMARY OF THE INVENTION

It is therefore an object of the present invention to provide a connector assembly which overcomes the above shortcomings.

It is another object of the present invention to provide a connector assembly which securely connects and locks a surgical tool to a surgical instrument.

It is still a further object of the present invention to provide a connector assembly which securely locks the surgical tool to the surgical instrument without any special tools, equipment and the like.

It is also a further object of the present invention to provide a connector assembly which allows a surgeon to easily remove and replace the surgical tool during a surgical procedure.

In one aspect of the invention, a connector assembly is provided for connecting a surgical tool to a surgical instrument. The connector assembly includes an upper clamping plate and a lower clamping plate positioned between the upper clamping plate and a cam plug. A clamping rod is attached to the upper clamping plate and extends through a bore of the lower clamping plate and the cam plug. A cam lever has a cam surface and is pivotally attached to the clamping rod at an end remote from the upper clamping plate. The cam lever is pivotable between a first position and a second position. When in the first position, the cam surface contacts the cam plug and the cam lever moves the clamping rod which, in turn, positions the upper clamping plate into the first locked position. The cam lever is also used to release the upper clamping plate to the second unlocked position remote from the lower clamping plate when pivoted to the second position.

In another aspect of the present invention, a surgical instrument is provided. The surgical instrument includes a housing, a motor positioned within the housing and a connector assembly for clamping a surgical tool to the housing. The connector assembly includes an upper clamping plate movable between a first locked position and a second unlocked position, a cam plug and a pivot assembly. The pivot assembly has a centrally located shaft with a longitudinal bore disposed therethrough, and a lower clamping plate positioned on the centrally located shaft such that a bore of the lower clamping plate is in alignment with the bore of the centrally located shaft. A plurality of teeth extend from the centrally located shaft. A clamping rod is attached to the upper clamping plate and extends through the bores. A cam lever is pivotally attached to the clamping rod and is pivotable between a first position and a second position. An oscillating jaw yoke having a bore with extending teeth meshes with the teeth of the pivot assembly.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF THE PREFERRED EMBODIMENT OF THE INVENTION

The present invention is directed to a connector assembly for connecting a surgical saw blade and more particularly a oscillating saw blade to a housing of a surgical instrument. The connector assembly is a keyless system which uses a cam and lever mechanism to securely connect the surgical saw blade including, for example, a sternum saw blade, to the surgical instrument. By using the connector assembly of the present invention, a surgeon or other medical personnel can firmly and securely lock the surgical blade in the connector assembly of the surgical instrument without any special tools, equipment and the like. This enables the surgeon or other medical personnel to easily remove and replace the surgical saw blade during a surgical procedure. The connector assembly of the present invention also allows the surgeon or other medical personnel to apply a high clamping force to the surgical blade with a relatively low actuation force.

Connector Assembly

Figure 1:
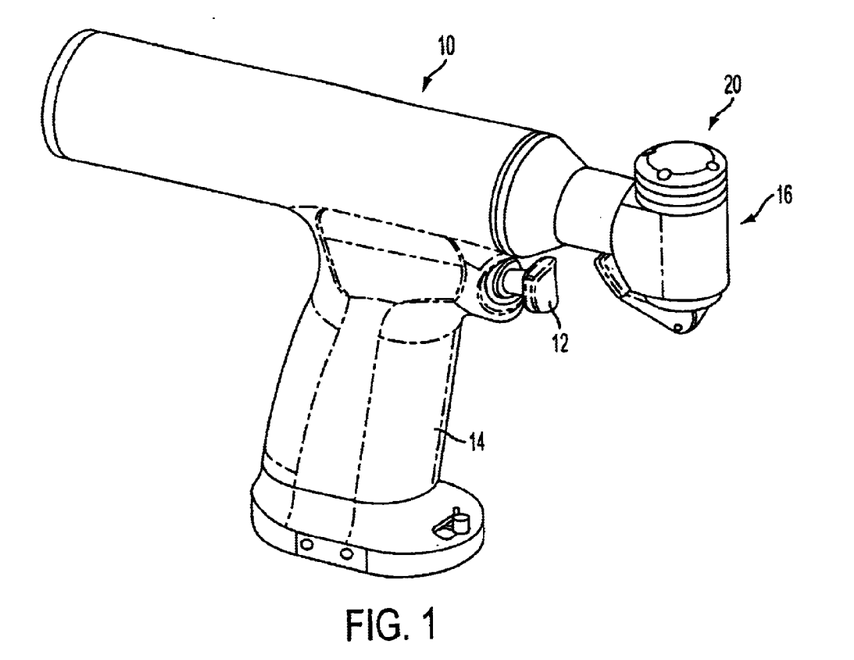
FIG. 1 shows a plan view of a surgical instrument using a connector assembly of the present invention.

Referring now to the drawings, and more particularly to FIG. 1, there is shown a plan view of a surgical instrument using a connector assembly of the present invention. More particularly, the surgical instrument includes a housing 10 which houses a motor or other driving device such as, for example, a reciprocating drive mechanism. The housing 10 is illustrated as a pistol grip type housing; however, other types of housing such as, for example, a wand type housing is also contemplated for use with the present invention. A trigger mechanism 12 and a grip portion 14 are provided on the housing 10. An output housing 16 extends from the housing 10 which houses the connector assembly, generally depicted as reference numeral 20, of the present invention. The connector assembly 20 is further described in more detail with reference to FIGS. 3–12. Speed controls (not shown) may also be provided on the housing 10.

Figure 2:
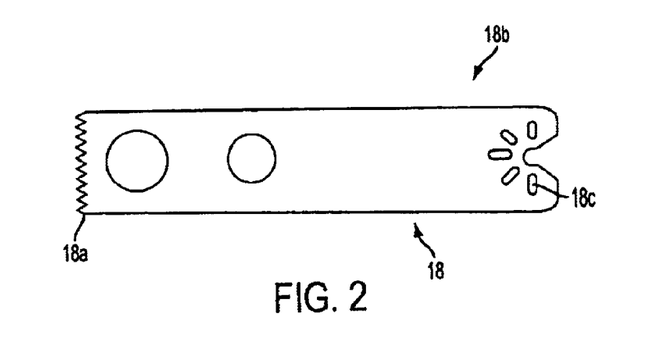
FIG. 2 shows a surgical tool used with the connector assembly.

FIG. 2 shows a surgical tool used with the connector assembly 20 of the present invention. The surgical tool is depicted as reference numeral 18 and is preferably a surgical saw blade. The surgical saw blade 18 includes a toothed portion 18a and a shank portion 18b with apertures 18c formed at an end opposing the toothed portion 18a. The apertures 18c may be formed in a pattern corresponding to locking pins extending from the connector assembly 20, as discussed below.

Figure 3:
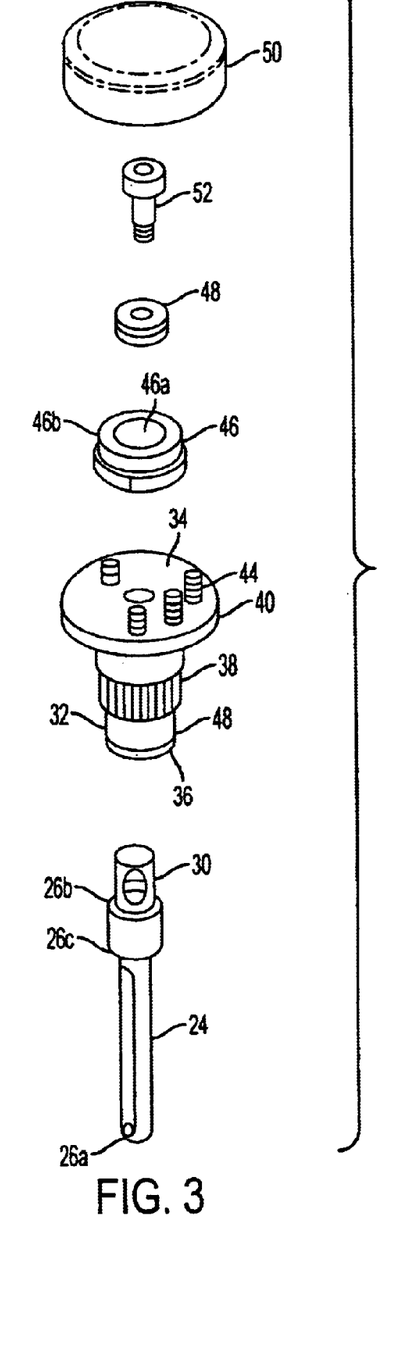
FIG. 3 shows an exploded perspective view of a jaw assembly used with the connector assembly of the present invention.

FIG. 3 shows an exploded perspective view of a jaw assembly 22 used with the connector assembly 20 of the present invention. As seen in this view, the jaw assembly 22 includes a clamping rod 24 having an aperture 26a at a first end and upper and lower shoulders 26b and 26c at a second end. The second end also includes a threaded hollow interior portion 30. The jaw assembly 22 further includes a pivot assembly 32 having a bore 34 disposed through a longitudinal axis thereof. The second end of the clamping rod 24 is slidably positioned within the bore 34 of the pivot assembly 32 such that the upper shoulder 26b of the clamping rod 24 abuts a shoulder 36 (shown in FIG. 4) of the pivot assembly 32 in an opened or unlocked position. (The shoulder arrangement provides a mechanism for maintaining an opened or unlocked position of the connector assembly.) The pivot assembly 32 further includes teeth 38 disposed at approximately a mid section thereof, and an upper plate 40 at a second end 42. At least one locking pin 44 extends upwards from the upper plate 40. An annular groove 48 is positioned about a first end 36 of the pivot assembly.

Still referring to FIG. 3, a jaw 46 is disposed on the upper plate 40 and a bearing 48 is disposed within an aperture 46a of the jaw 46. The jaw 46 further has an upward directing flange 46b. An upper clamping plate 50 is rotatably attached to the clamping rod 24 via a screw, bolt or other fastening device 52 which extends through the bore 34 (and the jaw 46 and bearing 48) of the pivot assembly 32.

Figure 4:
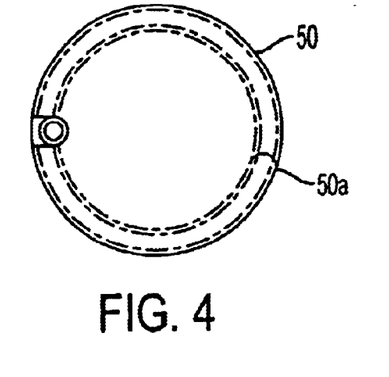
FIG. 4 shows an underside view of an upper clamping plate used with the jaw assembly.

FIG. 4 shows an underside view of the upper clamping plate 50. As seen in this view, the upper clamping plate 50 includes an annular groove 50a disposed about a circumference of the underside surface (i.e., the surface facing the upper plate 40) thereof. The annular groove 50a corresponds with the arrangement of the locking pins 44 extending from the upper plate 40 of the pivot assembly 32. In embodiments, the groove 50a may be of any shape and depth corresponding to any desired configuration or arrangement of locking pins 44 extending from the upper plate 40. Also, the groove 50a does not have to be a continuous groove, but may be separate indentations provided on the underside surface of the upper clamping plate 50.

Figure 5:
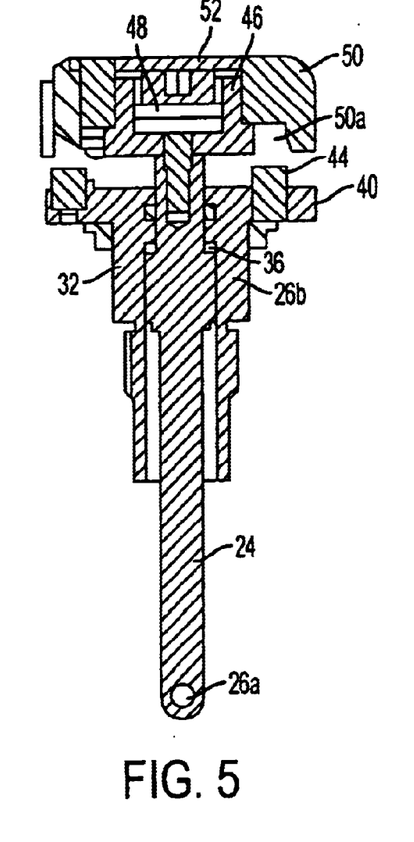
FIG. 5 shows a cut away view of an assembled jaw assembly in an open or unlocked position.

FIG. 5 shows a sectional view of the assembled jaw assembly 22 in an open or unlocked position. In this view, the bore 34 of the pivot assembly 32 is shown to include the shoulder 36. In the this opened or unlocked position, the shoulder 36 of the bore 34 is proximate to or abuts the shoulder 26b on the clamping rod 24. This provides for the height of the upper clamping plate 50 relative to the upper plate 40 of the pivot assembly 32. This view also shows the grooves 50a aligned with the locking pins 44.

Figure 6:
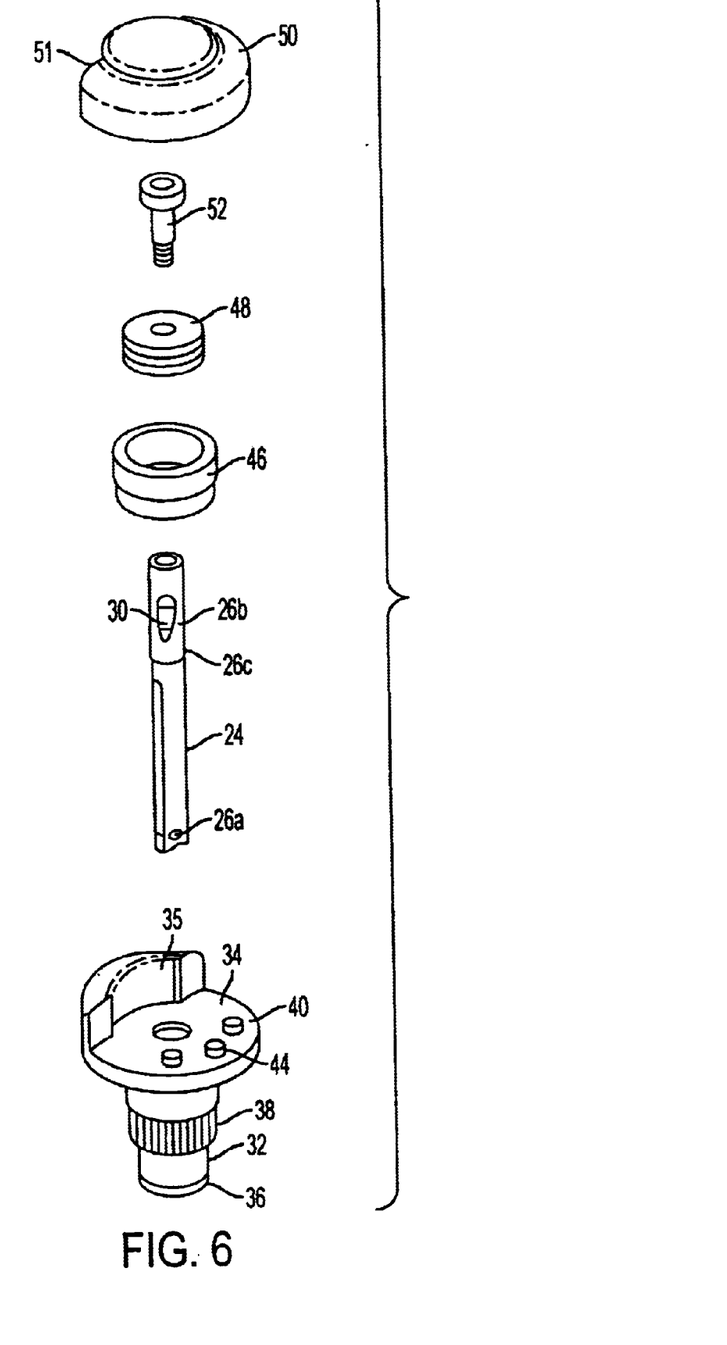
FIG. 6 shows an exploded perspective view of another embodiment of the jaw assembly used with the connector assembly of the present invention.

FIG. 6 shows an exploded perspective view of another embodiment of the jaw assembly 22 used with the connector assembly 20 of the present invention. For simplicity, the same reference numerals are used to describe the jaw assembly 22 of FIG. 6. As seen, the jaw assembly 22 includes the clamping rod 24 having the aperture 26a at a first end and the lower shoulder 26c at the second end; however, the clamping rod of FIG. 6 does not include the upper shoulder 26b. The second end of the clamping rod 24 also includes the threaded hollow interior portion 30. The jaw assembly 22 further includes the pivot assembly 28; however, in the embodiment of FIG. 6, the pivot assembly 28 includes a collar 35 which extends from the upper plate 40. The pivot assembly 32 further includes locking pins 44 about a portion of the circumference of the upper plate 40. The locking pins 44 should correspond in number and arrangement to the apertures located on the surgical saw tool used with the connector assembly 20 of the present invention. The upper clamping plate 50 is attached to the clamping rod 24 via a screw, bolt or other fastening device 52 which extends through the bore 34 (and the jaw 46 and bearing 48) of the pivot assembly 32. In the upper clamping plate 50 of FIG. 6, the upper clamping plate 50 is partially cut away to form a surface 51 so that it may mate, abut or be positioned proximate to the collar 35. The positioning and arrangement of the surface 51 of the upper clamping plate 50 with the collar 35 keys (e.g., prevents rotation) the upper clamping plate 50 in position. All other features are the same as shown in FIG. 3.

Figure 7:
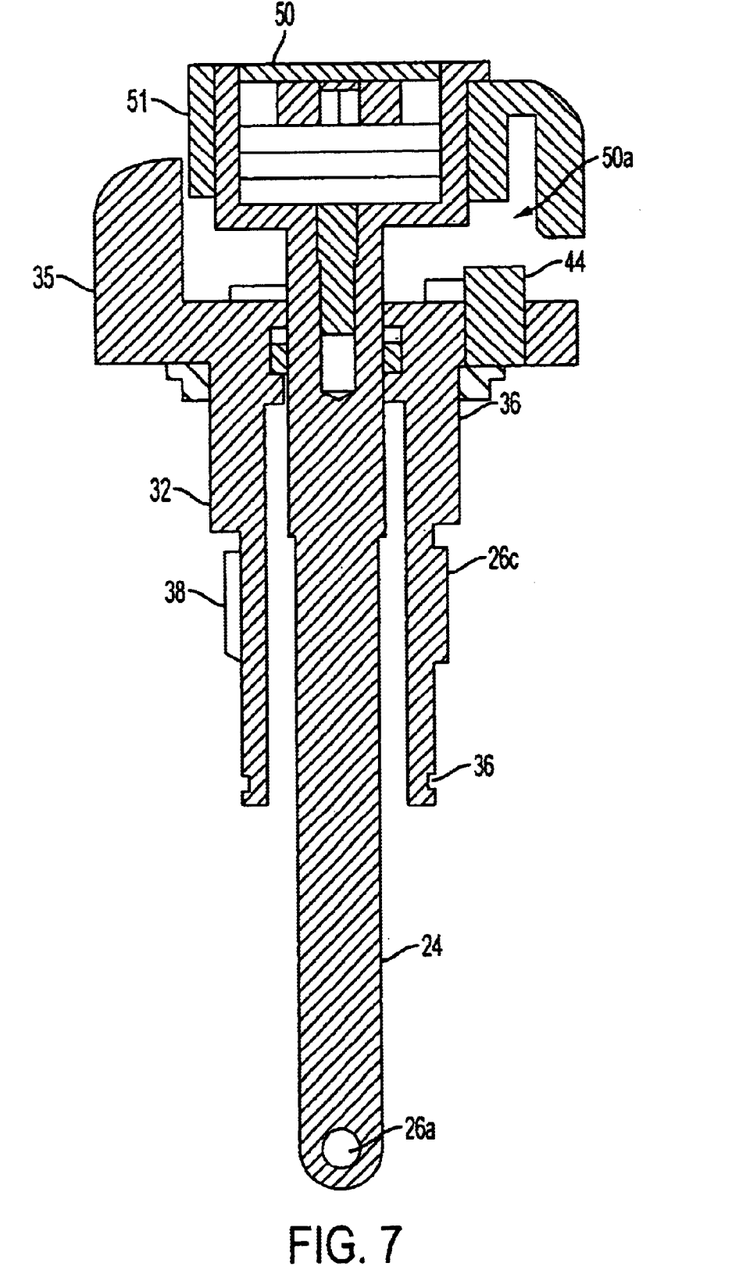
FIG. 7 shows the assembled jaw assembly of FIG. 6 in an open or unlocked position.

FIG. 7 shows the assembled jaw assembly 22 of FIG. 6 in an open or unlocked position. In the this opened or unlocked position, the collar 35 prevents the upper clamping plate 50 from rotating. This is due to the face 51 of the upper clamping plate 50 contacting or closely positioned near the collar 35. This view also shows the groove 50a aligned with the locking pins 44.

Figure 8:
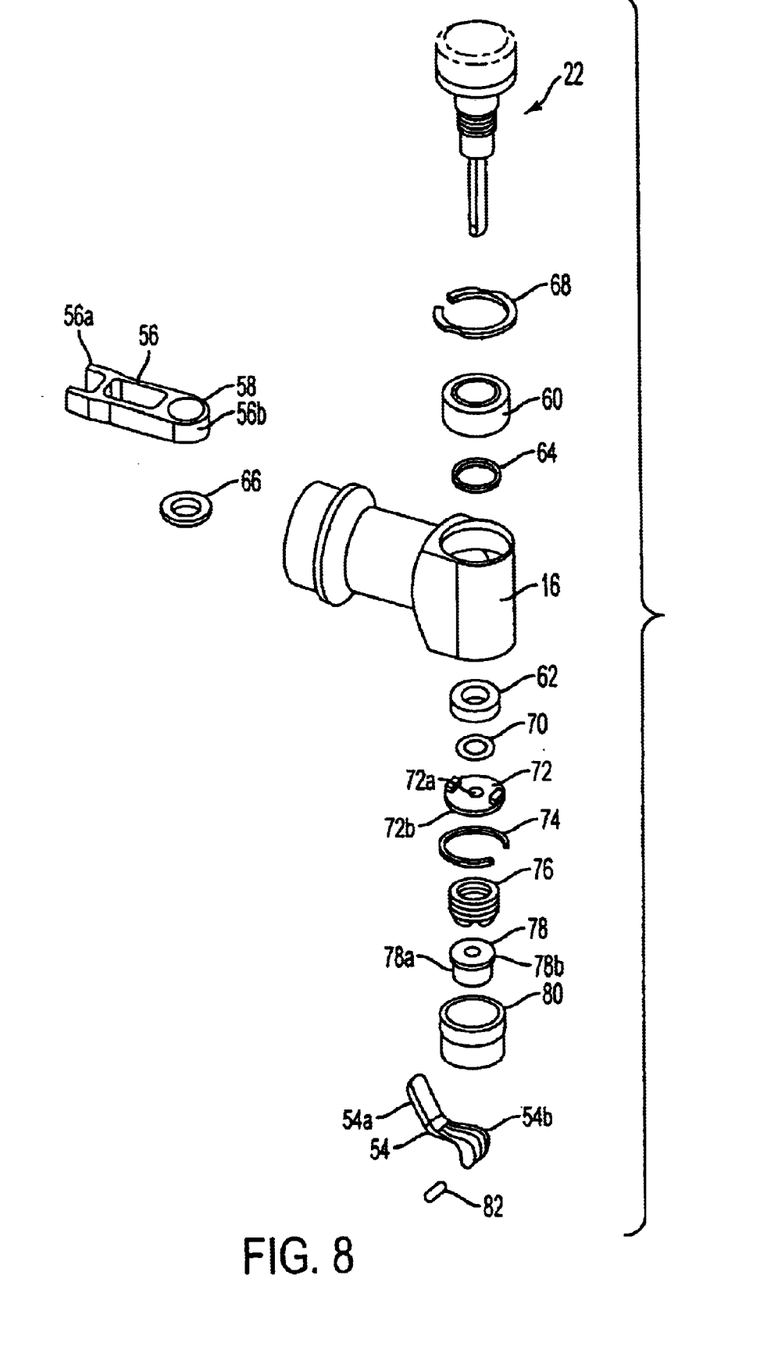
FIG. 8 shows an exploded perspective view of the connector assembly using the jaw assembly of FIG. 3.

FIG. 8 shows an exploded perspective view of the connector assembly 20 using the jaw assembly 22 of FIG. 3. The connector assembly 20 is partly housed within the output housing 16 of the surgical instrument, and includes a cam lever 54 pivotally attached to the jaw assembly 22. The cam lever 54 includes a lever or handle 54a and a cam surface 54b. An oscillating saw yoke 56 is disposed within the output housing 16, perpendicular to the jaw assembly 22. The oscillating saw yoke 56 includes a first end 56a which is connectable to an oscillating motor (not shown) and a second end 56b having a bore with a toothed surface 58. In the assembled structure (FIG. 9), the teeth 58 of the oscillating saw yoke assembly 56 mesh with the teeth 38 of the pivot assembly 32. In this manner, the rotation of the motor is translated into an oscillating movement of the saw blade 18.

Figure 9:
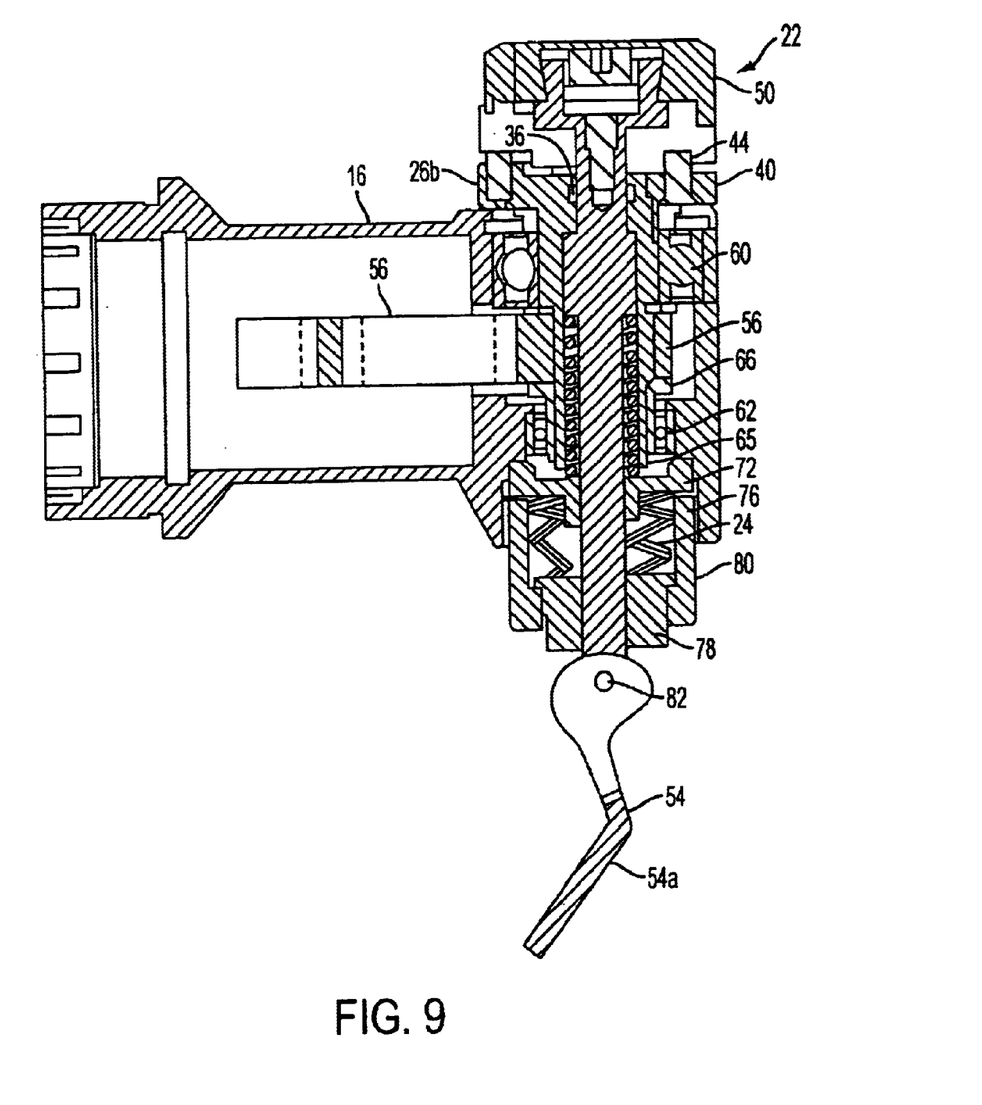
FIG. 9 shows a cut-away view of the connector assembly of FIG. 8 in an opened or unlocked position.

FIG. 8 further shows an upper bearing assembly 60 and a lower bearing assembly 62 positioned on respective upper and lower surfaces of the oscillating saw yoke 56. The bearing assemblies 60 and 62 and the oscillating saw yoke 56 are housed within the output housing 16. A washer 64 may be positioned between the upper bearing assembly 60 and the upper surface of the oscillating saw yoke 56. And, a yoke spacer 66 may be positioned between the lower surface of the oscillating saw yoke 56 and the lower bearing assembly 62. A first retention ring 68 is placed between the upper bearing assembly 60 and the jaw assembly 22, and a second retention ring 70 is placed below the lower bearing assembly 62. In the assembled structure (FIG. 10), the first retention ring 68 is secured to the output housing 16 and the second retention ring 70 engages the annular groove 36 of the pivot assembly 32 in order to retain the jaw assembly 22 to the oscillating saw yoke 56.

A key plate 72 is positioned adjacent to the lower bearing assembly 62 and a spiral retention ring 74 retains the key plate 72 adjacent to the lower bearing assembly 62. The key plate 72 includes an aperture 72a which substantially corresponds with the cross sectional shape of the clamping rod 24, and may include a downwardly extending flange 72b. A spring 65 (shown in FIGS. 9 and 10) is positioned between the lower shoulder 26c of the clamping rod 23 and the upper surface of the key plate 72. Also, a spring 76 is positioned and retained between the key plate 72 and a cam plug 78, on an opposing side of the key plate 72 with respect to the spring 65. The cam plug 78 includes a downward extending flange 78a and a shoulder 78b. The cam plug 78 is slidably positionable within a pivot plug 80 which includes an inwardly extending flange 80a. The shoulder 78b of the cam plug 78 is urged against the upwardly extending flange 80a, via the spring 76, when the connector assembly 20 is in an open or unlocked position (FIG. 9). The pivot plug 80 may be provided with a thread in order to secure the pivot plug 80 to the output housing 16 while retaining other components therein. The cam lever 54 is pivotally attached to the clamping rod 24 by placing a dowel pin 82 through the aperture 26a of the clamping rod 24.

FIG. 9 shows a cut-away view of the connector assembly 20 of FIG. 8 in an opened or unlocked position. In the unlocked position, the cam lever 54 is in a released position such that the cam surface 54b is positioned away from the surface of the cam plug 78. This allows the cam plug 78 to be urged downward by the spring 76 towards the cam surface 54b, but preferably not in contact therewith. In this position, the clamping rod 24 is urged upwards, through the bore 34 of the pivot assembly 32, by the spring 65. This is accomplished by the spring 65 biasing against the shoulder 26c of the clamping rod 24 and the key plate 72. The shoulder 26b of the clamping rod 24 abuts against the shoulder 36 in order to maintain a certain height or unlocked position of the upper clamping plate 50. The retention rings 68 and 70 maintain the position of the pivot assembly 32 within the output housing 16 in both the opened (unlocked) and closed (locked) position. The retention ring 70 also maintains the relative positions between the lower bearing assembly 68, the yoke spacer 66, the oscillating saw yoke 56 and the pivot assembly 32 within the output housing 16. Similarly, the retention ring 74 maintains the position of the key plate 72 within the output housing 16 in both the opened (unlocked) and closed (locked) position.

Figure 10:
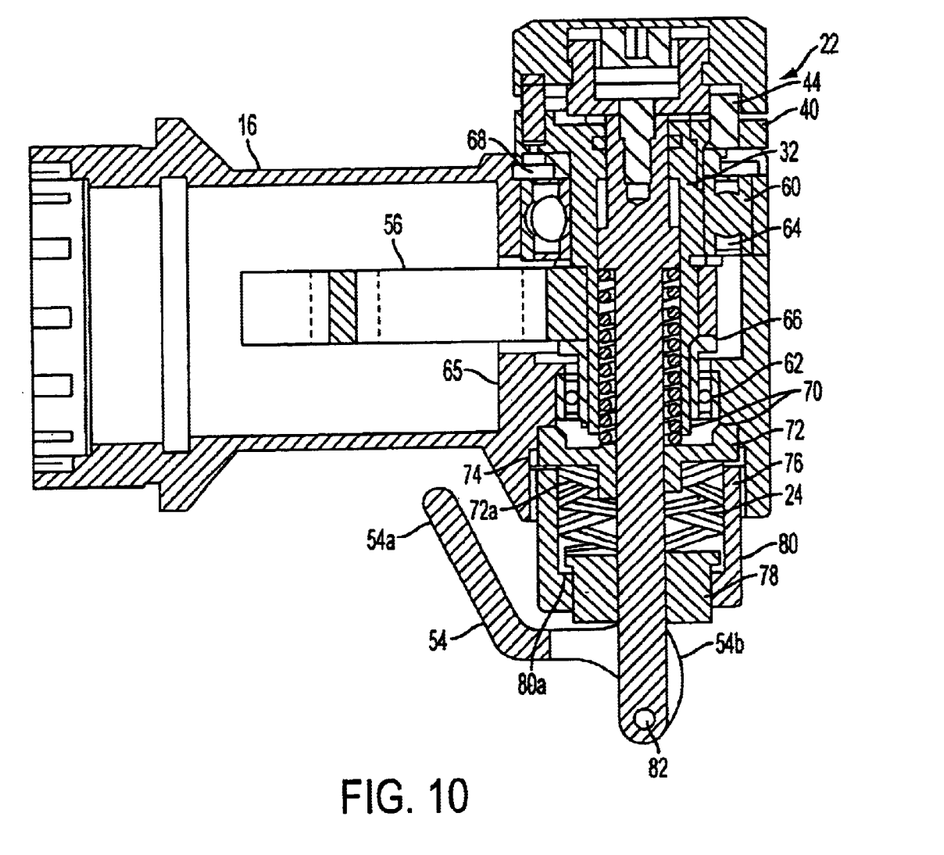
FIG. 10 shows a cut-away view of the connector assembly of FIG. 8 in a closed or locked position.

FIG. 10 shows a cut-away view of the connector assembly 20 of FIG. 8 in a closed or locked position. In the locked position, the cam surface 54b of the cam lever 54 abuts against the surface of the cam plug 78. This forces the cam plug 78 slightly upwards toward the key plate 72 (compressing the spring 76) and the upper clamping plate 50 downward (or in the opposite direction) towards the pivot assembly 32 (compressing the spring 65). In this position, the clamping rod 24 is also forced downward, moving through the bore 34 of the pivot assembly 32. In this closed or locked position, the locking pins 44 engage the annular groove 50a as well as the apertures 18c of the saw blade 18 to hence securely retain the saw blade therein. In this position, the spring 65 is compressed between the lower shoulder 26c of the clamping rod 26 and the upper surface of the key plate 72, and the spring 76 is compressed between the pivot plug 80 and the lower surface of the key plate 72. The spring 76 may be positioned about a downward flange 72a of the key plate 72. The spring 65 will urge the clamping rod 24 and hence the upper clamping plate 50 upwards to disengage the locking pins 44 from the groove 50a when the cam lever 54 is released. At this time of release, the spring 76 will also urge the cam plug 78 downwards, in the opposite direction of the clamping rod 24 and upper clamping plate 50.

Figure 11:
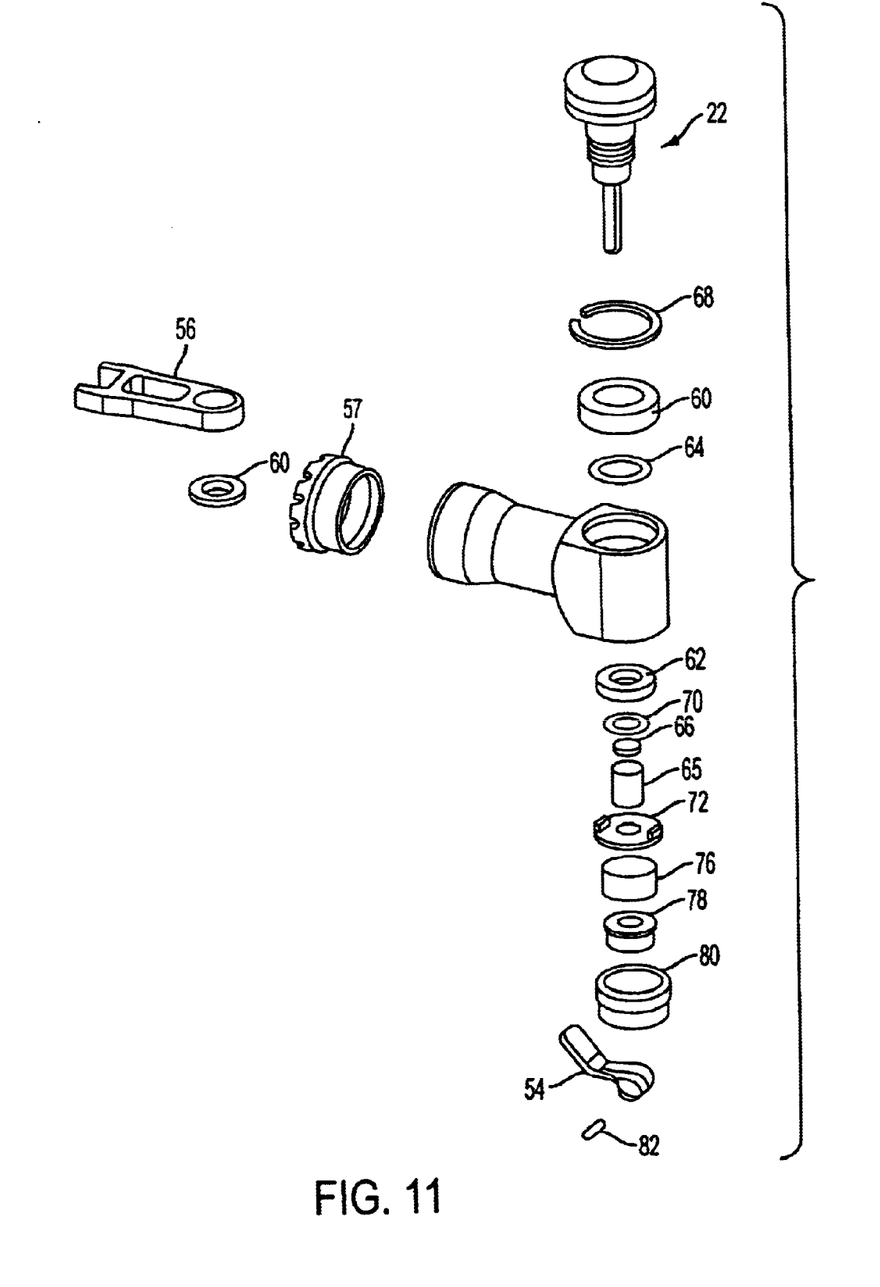
FIG. 11 shows an exploded perspective view of the connector assembly using the jaw assembly of FIG. 6.

FIG. 11 shows an exploded perspective view of the connector assembly 20 using the jaw assembly 22 of FIG. 6. In this assembly, a washer 63 is positioned between the spring 65 and the lower bearing assembly 62. Also, a collar assembly 57 is placed at an end of the output housing 16 which is mounted to the housing. All the remaining features of the connector assembly 20 are described with reference to the connector assembly 20 shown in FIG. 8.

Figure 12:
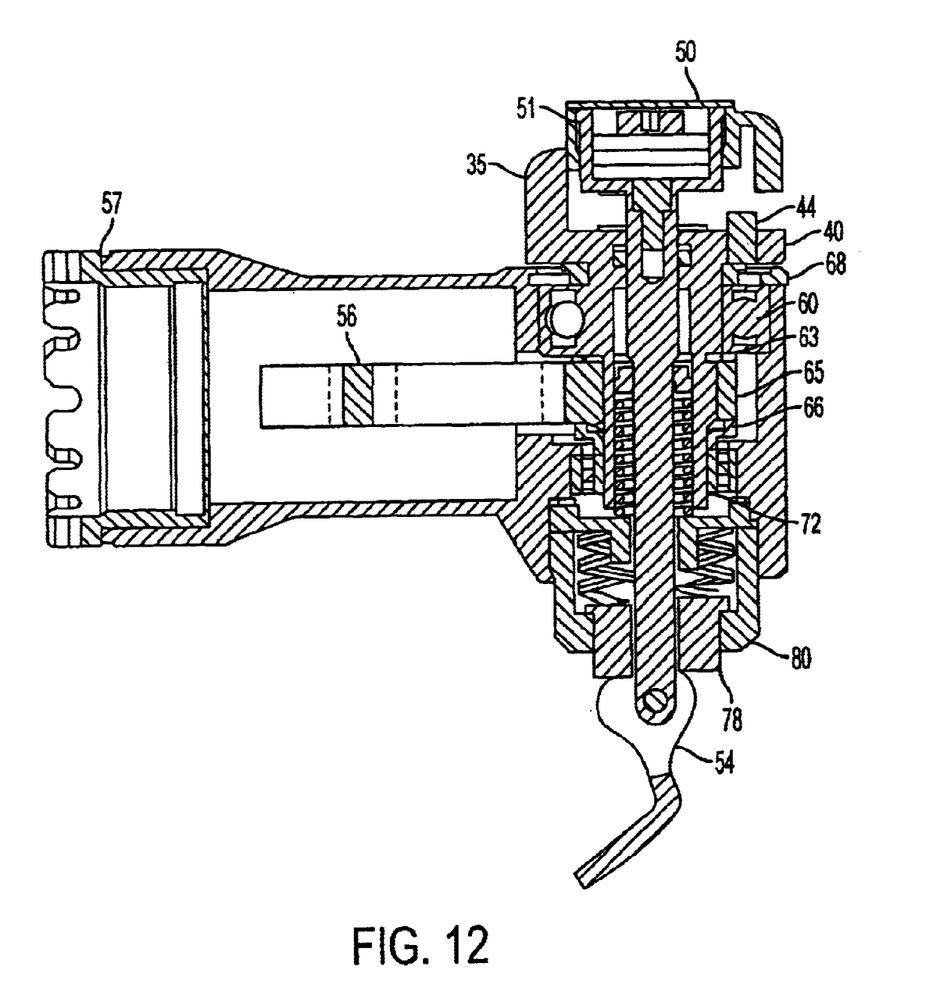
FIG. 12 shows a cut-away view of the connector assembly of FIG. 11 in an opened or unlocked position.

FIG. 12 shows a cut-away view of the connector assembly 20 of FIG. 11 in an opened or unlocked position. In the unlocked position, the cam lever 54 is in a released position such that the cam surface 54b remains in contact with the surface of the cam plug 78. This maintains the height or open position of the upper clamping plate 50. The cam plug 78 is urged downward by the spring 76 towards the cam surface 54b. In this unlocked position, the clamping rod 24 is urged upwards, through the bore 34 of the pivot assembly 32, by the spring 65. This is accomplished by the spring 65 biasing against the washer 63 (which, in turn, abuts the shoulder 26c of the clamping rod 24) and the key plate 72. The contact between the cam plug 78 and the cam surface 54b will maintain the height of the cap jaw 50 relative tot he upper plate 44 in the open or unlocked position. The retention rings 68 and 70 maintain the position of the pivot assembly 32 within the output housing 16 in both the opened (unlocked) and closed (locked) position. The retention ring 70 also maintains the relative positions between the lower bearing assembly 68, the yoke spacer 66, the oscillating saw yoke 56 and the pivot assembly 32 within the output housing 16. Similarly, the retention ring 74 maintains the position of the key plate 72 within the output housing 16 in both the opened (unlocked) and closed (locked) position. The collar 35 prevents the upper clamping plate 50 from rotating in the opened position, and maintains the upper clamping plate 50 in a keyed position so that it maintains an alignment with the pivot assembly, and more specifically the groove or indentations 50a maintain an alignment with the locking pins 44.

Method of Inserting the Surgical Tool into the Connector Assembly

Prior to inserting the surgical tool into the connector assembly 20 of the present invention, the cam lever 54 is positioned in a released position such that the cam plug 78 is urged downward by the spring 76 towards the cam surface 54b and the clamping rod 24 is urged upwards, through the bore 34 of the pivot assembly 32, by the spring 65. In this position, the upper clamping plate 50 is positioned remotely (i.e., spaced apart) from the pivot assembly 32. The surgical tool is then inserted between the upper clamping plate 50 and the pivot assembly 32 with the apertures of the surgical tool aligned with the locking pins 44. An actuation force is then applied to the cam lever 54 in order to (i) force the upper clamping plate 50 downwards toward the upper plate 40 of the pivot assembly 32 and (ii) the cam plug 78 slightly upwards. The upper clamping plate 50 is forced downward via the translation of movement from the cam surface 54b of the cam lever 54 through the clamping rod 24 which, in turn, is attached to the upper clamping plate 50. The forcing downward of the upper clamping plate 50 clamps the surgical tool between the upper plate 40 and the upper clamping plate 50 of the jaw assembly 22, thereby securely fastening the surgical tool to the connector assembly 20 of the present invention.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A connector assembly comprising:
   an upper clamping plate movable between a first locked position and a second unlocked position;
   a cam plug;
   a lower clamping plate positioned between the upper clamping plate and the cam plug;
   a clamping rod attached to the upper clamping plate and extending through a bore of the lower clamping plate and the cam plug; and
   a cam lever having a cam surface, the cam lever being pivotally attached to the clamping rod at an end remote from the upper clamping plate, the cam lever being pivotable between a first position and a second position,
   wherein when the cam lever is pivoted to the first position the cam surface contacts the cam plug and the cam lever moves the clamping rod which positions the upper clamping plate into the first locked position proximate, and releases the upper clamping plate to the second unlocked position remote from the lower clamping plate when pivoted to the second position.

2. The connector assembly of claim 1, wherein the cam surface contacts the cam plug when the cam lever is in the second position in order to maintain a predetermined height of the upper clamping plate with respect to the lower clamping plate when the upper clamping plate is in the second unlocked position.

3. The connector assembly of claim 1, further comprising a collar extending upward from the lower clamping plate proximate to the upper clamping plate, the collar restricting a rotation of the upper clamping plate.

4. The connector assembly of claim 1, further comprising:
   a key plate;
   shoulder on the clamping rod;
   a washer abutting the shoulder of the clamping rod; and
   a spring positioned between the key plate and the washer, the spring biasing the upper clamping plate to the second unlocked position when the cam lever is in the second position.

5. The connector assembly of claim 1, further comprising:
   a key plate;
   a shoulder on the clamping rod;
   a washer abutting the shoulder of the clamping rod; and
   a spring positioned between the key plate and the washer, the spring biasing the upper clamping plate to the second unlocked position when the cam lever is in the second position,
   wherein the cam surface contacts the cam plug when the cam lever is in the second position in order to maintain a predetermined height of the upper clamping plate with respect to the lower clamping plate when the upper clamping plate is in the second unlocked position.

6. The connector assembly of claim 1, further comprising:
   a groove or one or more indentations on an underside surface of the upper clamping plate facing the lower clamping plate; and
   at least one locking pin extending upwards from the lower clamping plate corresponding in arrangement to the groove or the one or more indentations,
   wherein the at least one locking pin engages the groove or the one or more indentations when the upper clamping plate is in the first locked position.

7. The connector assembly of claim 1, further comprising:
   a pivot assembly including:
      a centrally located shaft;
      a bore disposed through a longitudinal axis of the centrally located shaft;
      the lower clamping plate positioned on the centrally located shaft, the bore of the lower clamping plate aligning with the bore of the centrally located shaft; and
      a plurality of teeth positioned at an approximate mid section of the centrally located shaft,
   wherein the clamping rod is slidably positioned within the bore of the centrally located shaft.

8. The connector assembly of claim 7, wherein:
   the bore of the centrally located shaft includes a shoulder; and
   the clamping rod includes a shoulder, the shoulder of the clamping rod abuts the shoulder of the bore of the centrally located shaft when the upper clamping plate is in the second unlocked position in order to maintain a predetermined height of the upper clamping plate with respect to the lower clamping plate.

9. The connector assembly of claim 1, further comprising a spring between the upper clamping plate and the cam plug for urging the upper clamping plate into the second unlocked position when the cam lever is in the second position.

10. The connector assembly of claim 1, further comprising
   a key plate;
   a first shoulder and a second shoulder on the clamping rod; and
   a spring positioned between the key plate and the first shoulder, the spring biasing the upper clamping plate to the second unlocked position when the cam lever is in the second position.

11. The connector assembly of claim 10, further comprising a second spring positioned between the key plate and the cam plug, the second spring biasing the cam plug towards the cam surface when the cam lever is in the second position, the second spring being compressed when the cam lever is in the first position.

12. The connector assembly of claim 1, further comprising:
   an oscillating saw yoke having a bore with extending teeth;
   a pivot assembly, the pivot assembly including:
      a centrally located shaft;
      a bore disposed through a longitudinal axis of the centrally located shaft;
      the lower clamping plate positioned on the centrally located shaft, the bore of the lower clamping plate aligning with the bore of the centrally located shaft; and
      a plurality of teeth positioned at an approximate mid section of the centrally located shaft,
   wherein the oscillating saw yoke extending teeth mesh with the teeth of the pivot assembly.

13. The connector assembly of claim 1, further comprising a retention ring for holding the lower clamping plate stationary.

14. A surgical instrument, comprising:
   a housing;
   a motor positioned within the housing;
   a connector assembly for clamping a surgical tool to the housing, the connector assembly including:
      an upper clamping plate movable between a first locked position and a second unlocked position;
      a cam plug;
      a pivot assembly, the pivot assembly including:
         a centrally located shaft;
         a bore disposed through a longitudinal axis of the centrally located shaft;
         a lower clamping plate having a bore and being positioned on the centrally located shaft, the bore of the lower clamping plate aligning with the bore of the centrally located shaft; and
         a plurality of teeth positioned at an approximate mid section of the centrally located shaft;
      a clamping rod attached to the upper clamping plate and extending through the bore of the lower clamping plate and the cam plug;
      a cam lever having a cam surface, the cam lever being pivotally attached to the clamping rod at an end remote from the upper clamping plate, the cam lever being pivotable between a first position and a second position; and
   an oscillating saw yoke having a bore with extending teeth, the oscillating saw yoke extending teeth meshing with the teeth of the pivot assembly.

15. The surgical instrument of claim 14, wherein when the cam lever is pivoted to the first position the cam surface contacts the cam plug and the cam lever moves the clamping rod which positions the upper clamping plate into the first locked position proximate, and releases the upper clamping plate to the second unlocked position remote from the lower clamping plate when pivoted to the second position.

16. The surgical instrument of claim 14, wherein the oscillating saw yoke connects to the motor in order to oscillate the pivot assembly.

17. The surgical instrument of claim 14, wherein the cam surface contacts the cam plug when the cam lever is in the second position in order to maintain a predetermined height of the upper clamping plate when in the second unlocked position.

18. The surgical instrument of claim 17, further comprising:
   a key plate;
   a shoulder on the clamping rod;
   a washer abutting the shoulder of the clamping rod; and
   a spring positioned between the key plate and the washer, the spring biasing the upper clamping plate to the second unlocked position when the cam lever is in the second position.

19. The connector of claim 14, further comprising:
   a collar extending upward from the lower clamping plate proximate to the upper clamping plate, the collar restricting a rotation of the upper clamping plate;
   a groove or one or more indentations on an underside surface of the upper clamping plate facing the lower clamping plate; and
   at least one locking pin extending upwards from the lower clamping plate corresponding in arrangement to the groove or the one or more indentations, the at least one locking pin engaging the groove or the one or more indentations when the upper clamping plate is in the first locked position.

20. The connector assembly of claim 19, wherein:
   the bore of the centrally located shaft includes a shoulder; and
   the clamping rod includes a shoulder, the shoulder of the clamping rod abuts the shoulder of the bore of the centrally located shaft when the upper clamping plate is in the first opened position in order to maintain a predetermined height of the upper clamping plate with respect to the lower clamping plate.

* * * * *